United States Patent [19]

Firshein

[11] Patent Number: 6,121,245

[45] Date of Patent: Sep. 19, 2000

[54] METHOD OF TREATING CANCER USING ALKYLGLYCEROLS IN CONJUNCTION WITH CHEMOTHERAPY

[76] Inventor: Richard N. Firshein, 1230 Park Ave., New York, N.Y. 10128

[21] Appl. No.: 08/791,757

[22] Filed: Jan. 29, 1997

[51] Int. Cl.[7] .................. A61K 31/70; A61K 31/505; A61K 31/335; A61K 33/24
[52] U.S. Cl. ..................... 514/34; 514/274; 514/449; 424/649
[58] Field of Search ........................... 514/34, 274, 449; 424/649

[56] References Cited

U.S. PATENT DOCUMENTS

| | | | |
|---|---|---|---|
| 3,432,602 | 3/1969 | Brohult et al. | 424/307 |
| 4,046,914 | 9/1977 | Hallgreen et al. | 424/312 |
| 4,837,023 | 6/1989 | Eibl et al. | 424/439 |
| 5,633,285 | 5/1997 | Martin | 514/724 |

OTHER PUBLICATIONS

Brohult et al., Acta Obstet Gynecol Scand, 65:779–785 (1986) (Exhibit 1).

Brohult et al., Acta Obstet Gynecol Scand, 57:79–83 (1978) (Exhibit 2).

Brohult et al., Acta Chem. Scand., 24(2):730–732 (1970) (Exhibit 3).

Burns and Spector, Nutrition Reviews, 48(6):233–240 (1990) (Exhibit 4).

Clandinin et al., The Journal of Pediatrics, 125(5):S25–S32 (1994) (Exhibit 5).

Das et al., Lipids, 27(6):401–405 (1992) (Exhibit 6).

Lissner et al., Acta Obstet Gynecol Scand, 72:481–487 (1993) (Exhibit 7).

*Primary Examiner*—Jerome D. Goldberg
*Attorney, Agent, or Firm*—Gary J. Gershik; Cooper & Dunham LLP

[57] ABSTRACT

Tumor cell kill is increased and the sensitivity of tumors to chemotherapeutic agents is increased by the administration of an alkylglycerol together with the chemotherapeutic agent.

14 Claims, 2 Drawing Sheets

METHOD OF TREATING CANCER USING ALKYLGLYCEROLS IN CONJUNCTION WITH CHEMOTHERAPY

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Alkylglycerols are lipids with a glycerol backbone, to which fatty acid derivatives are coupled by means of an ether bond instead of the ester bond that characterizes most mono-di-and triglycerides and related phospholipids. The ether lipids are present in high concentrations in human bone marrow, spleen and liver (Horrocks, 1972). They contain both saturated and mono-unsaturated 16- and 18- carbon fatty acids. Some are methyl/methoxy-substituted at the fatty acid in the 1-position (Boeryd et al.) or in the 2-position. (Hermann et al.)

The naturally occurring alkylglycerols are in most cases esterified with fatty acids of 16–18 C-atoms, sometimes unsaturated. It is of interest to point out the similarity in size and structure between these esters and the triglycerides.

| | |
|---|---|
| $CH_2.OH$ | $CH_2.OH$ |
| $CH.OH$ | $CH.OH$ |
| $CH_2.OH$ | $CH_2.O.R.$ |
| Glycerol | Alkylglycerol |
| $CH_2.O.CO.R$ | $CH_2.O.CO.R$ |
| $CH.O.CO.R.$ | $CH.O.CO.R$ |
| $CH_2.O.CO.R$ | $CH_2.O.R$ |
| Triglyceride | Alkylglycerol ester |

Sandler was the first to show that treatment with the alkylether batyl alcohol had a hematopoietic effect in rats as well as in human subjects. His results have been confirmed by Arturson and Lindback, who found that mice treated with batyl alcohol showed an increase both in the erythrocyte and in the reticulocyte count.

Brohult and Holmberg (1954) used the unsaponifiable portion of different bone marrow fats as well as preparations containing esters of alkylglycerols in child leukemia. A maturing effect on the white blood cells was observed. This preliminary investigation was followed up by experiments employing alkylglycerols in irradiation leucopenia. (Alexander et al., 1959)

In 1963 Astrid Brohult published a thesis on alkylglycerols and their use in radiation treatment. The alkylethers used were isolated from Greenland shark liver (Somniosus microcephalus) by molecular distillation followed by hydrolysis.

In patients with uterine cancer it was shown that the decrease in white cells and thrombocytes which usually occurs during radiation treatment is less pronounced if alkylglycerols are administered during this treatment.

In experiments on irradiated rats, it was shown that alkylglycerols or their esters inhibit, to a certain extent, the decrease of both megacaryocytes and nucleated cells in the bone marrow in connection with irradiation.

In 1977 it was shown that the incidence of injuries following radiation therapy for carcinoma of the uterine cervix was significantly decreased when the patients were treated with alkylglycerols. (Brohult et al.) In 1979 it was shown that the frequency of severe fistulas (recto-vaginal and vesico-vaginal) was reduced by 47% when alkylglycerols were administered prior to radiation treatment. (Brohult et al.)

The aim of Brohult's early investigations was to study the effect of alkyldiacylglycerols on granulocytopenia after radiation. When the results were analyzed later, it was found that patients given alkyldiacylglycerols had a higher survival rate than the controls. When comparing the groups, standardized proportions of stages were used. The radiation treatment was the same for the two groups. After 3 years, the group treated with alkyldiacylglycerols showed a higher survival rate that the controls, and after 5 years the survival rate was still higher, and the difference was significant ($p < 0.05$). It is interesting to note that the survival rate was higher for all tumor stages in patients treated with ether lipids than in the corresponding control groups.

In a double-blind study performed in 1970–1972, there was a tendency toward lower stages in patients treated with alkylglycerols in comparison to controls, and a study carried out in the years 1973–1975 also showed a shift to lower stages in the prophylactically treated patients. (Brohult et al., 1986)

When all groups of patients with uterine cancer are put together (1964–1966, 1970–1972, 1973–1975) the total amount of patients studied consists of 841 prophylactically treated cases and 4404 control cases (=usual radiation therapy without alkoxyglycerol treatment). The mortality after five years in the prophylactic group was 31.0 percent while the mortality in the corresponding control group was 39.6 per cent. The difference is statistically significant ($p < 0.001$). (Brohult et al., 1986)

In a study by Brohult et al 1972 it was observed that patients vaccinated against typhoid-paratyphoid before implantation of radium for uterine cancer and given alkylglycerols produced antibodies to a larger extent than a control group receiving radiation treatment but not alkoxyglycerols.

In animal experiments it has been shown (Boeryd et al, 1978, 1980) that methoxy-substituted alkylglycerols in the feed stimulates the immune reactivity in mice against red blood cells as determined by the number of plaque-forming cells. Further the methoxy-substituted alkylglycerols stimulated cellular immunoreactivity as demonstrated by the increased ability of parenteral spleen cells to endure a graft-versus-host reaction in hybrid mice.

About 2% of the alkylglycerols in the Greenland shark liver oil consists of methoxy-substituted alkylglycerols with the methoxy group in the 1-position.

Chemotherapy for cancer has essentially remained the same for the last twenty years. There have been several variations of the standard CMF, CMFVP, CMFT, and CAF, but no breakthrough in new modalities or combination treatments that have yet proven effective.

Since no chemotherapy combination has improved survival, it seems reasonable to attempt to modify the milieu that the tumor presided in. Burns and Spector's findings suggested a potential role for lipid nutrition in cancer therapy. It has been well documented that fatty acid content of cancer cell membranes can change substantially when the cells are exposed to different types of fat. Certain physical and functional properties of the membrane are modified making the cells more sensitive to treatment of doxorubicin. The purpose of this study was to evaluate the use of Alkylglycerols in the treatment of cancer by examining its effect on inhibiting cellular growth and augmenting cytotoxic effects of chemotherapeutic agents.

The increasing incidence of cancer may be related to our diet which is high in saturated fats and vegetable oil. Lissner et al. have shown that the type of fat consumed influences the occurrence of endometrial cancer. Shu et al. found in a study in China that diets high in animal fat may play an important role in the ideology of endometrial cancer. A review in the British Medical Journal by Austoker et al concluded that diet is a major factor in the aetiology of cancer of the large bowel and stomach. Zhang et al. concluded that high fat intake is associated with reduced survival in post menopausal women with breast cancer.

Methoxy-substituted alkylglycerols have been shown to inhibit tumor growth in cultured cell lines. (Hallgrasen et al., 1978). Recent studies postulate that these substances can both stimulate the immune system and inhibit tumors.

Alkylglycerols may exert their beneficial effects by modifying membrance structure and function and by altering signal transduction. Membrane fatty acids can be altered by diet in animals. Such modifications can alter the membrane fluidity and possibly alter the cellular transport mechanisms. Sebokova concluded in rat models that the changes in the type of oil administered to rats changed plasma membrane contents and binding capacities of the gonadotropin receptor. Other studies by Luo et al found that dietary (n-3) polyunsaturated fatty acids changed membrane potentials. Clandinin et al questioned whether diet could be used to induce formation of membrane structures that are more resistant to specific insults through the use of omega-3 fatty acids.

Differences in the rate of cancer incidence among different countries and the corresponding changes in the incidence of cancer in people who migrate from an area of lower incidence to an area of higher incidence where the diet differs, suggest that environmental factors, e.g., dietary fat, might play a role in the occurrence of this disease. Numerous epidemiological studies suggest there is an association of dietary fat with breast cancer risk and survival from breast cancer after treatment. Holm et al concluded that dietary intervention might serve as an adjuvant treatment to improve breast cancer prognosis, particularly in patients with ER-rich breast cancers. Dietary fat may have an effect on growth or spread of breast cancer, both of which may vary in accordance with the type of fat. Animal studies by Rose et al found that the type of dietary fat directly effected the extent of metastasis, being highest in mice consuming omega-6 polyunsaturated fats.

SUMMARY OF THE INVENTION

The present invention provides a method of treating a malignant tumor comprising of malignant tumor cells in a subject by administering to the subject a chemotherapeutic agent and an alkylglycerol, each in an amount effective to kill malignant tumor cells or inhibit malignant tumor cell proliferation, thereby treating the tumor.

The present invention also provides a method of treating a malignant tumor comprising of malignant tumor cells in a subject by administering to the subject a compound having the formula

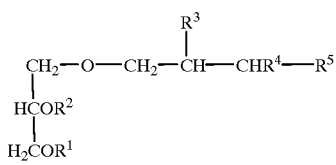

wherein $R^1$ and $R^2$ are the same or different and each is selected from the group consisting of hydrogen and aliphatic acyl groups of at most 24 carbon atoms, one of $R^3$ and $R^4$ is hydrogen and the other is selected from the group consisting of straight, branched, saturated and unsaturated alkoxy groups of at most 7 carbon atoms, and $R^5$ is selected from the group consisting of straight and branched alkyl and alkenyl groups of 4 to 21 carbon atoms; and a chemotherapeutic agent, each in an amount effective to kill malignant tumor cells or inhibit malignant tumor cell proliferation thereby treating the tumor.

DETAILED DESCRIPTION OF THE INVENTION

Figure 1:
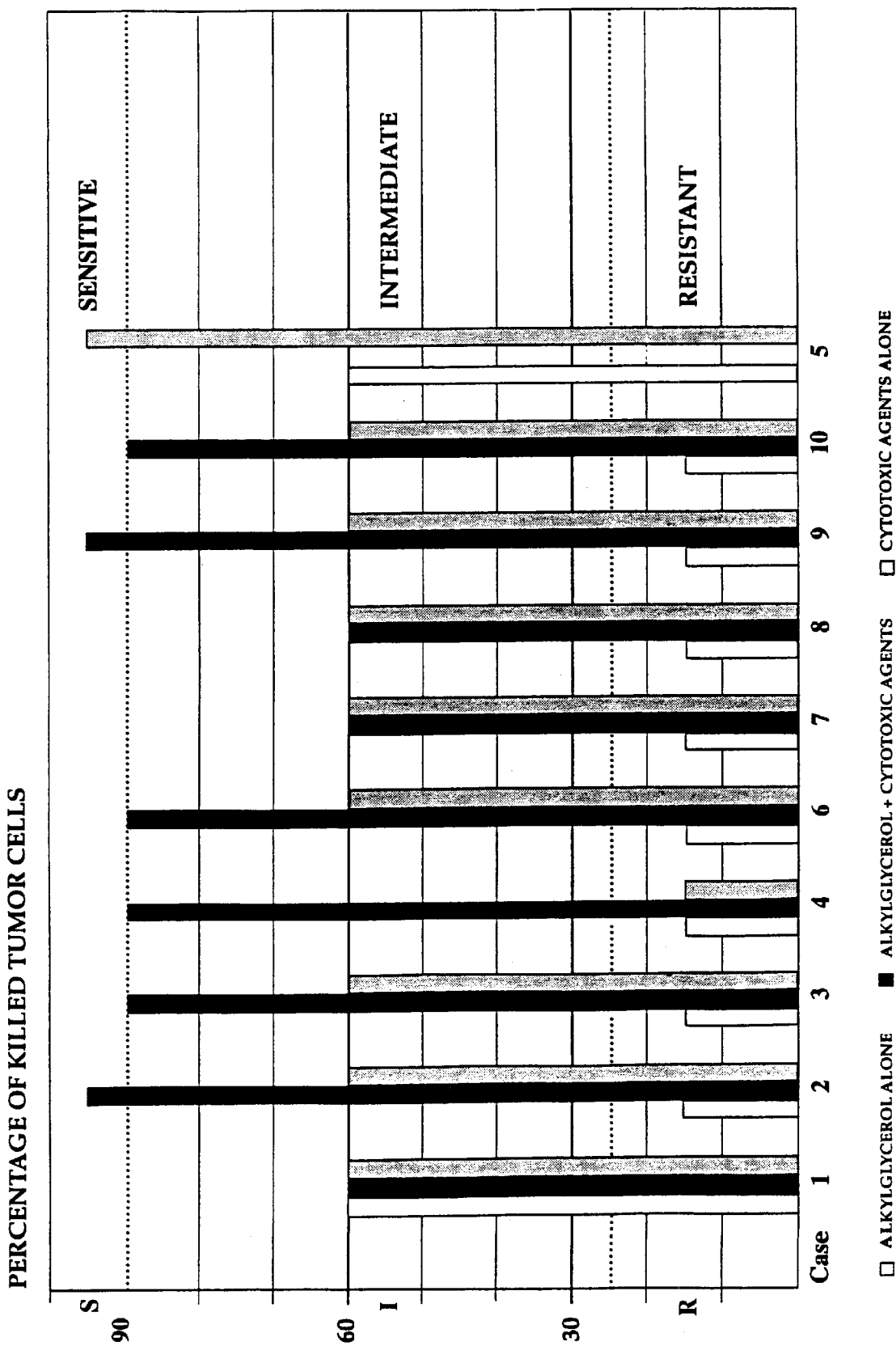
FIG. 1 shows the response of ten biopsies to chemotherapeutic agents alone as compared to alkylglycerol alone as compared to the combination of chemotherapeutic agent with the alkylglycerol.

The present invention provides a method of treating a malignant tumor comprising of malignant tumor cells in a subject by administering to the subject a chemotherapeutic agent and an alkylglycerol, each in an amount effective to kill malignant tumor cells or inhibit malignant tumor cell proliferation, thereby treating the tumor.

The tumor may be infiltrating duct carcinoma, adenocarcinoma or colon cancer.

In one embodiment of the invention, the subject is a mammal such as a human.

In a preferred embodiment the alkylglycerol is shark liver oil or a methoxy-substituted analog thereof.

In yet another embodiment more than one chemotherapeutic agent is administered and/or more than one alkylglycerol is administered.

In another embodiment the administration of the chemotherapeutic agent follows administration of the alkylglycerol.

In yet another embodiment of the chemotherapeutic agent is administered together with the alkylglycerol.

In another embodiment the administration of the alkylglycerol is intravenous, intramuscular, subcutaneous, topical, or intravenous in the form of a liposome.

In yet another embodiment the administration of the chemotherapeutic agent is oral, intravenous, intramuscular, intradermal, subcutaneous, topical, or intravenous in the form of a liposome.

In another embodiment the chemotherapeutic agent and/or the alkylglycerol is administered with or without a pharmaceutically acceptable carrier.

In yet another embodiment the effective amount of the alkylglycerol or an analog thereof is from about 1 g/Kg of body weight to 10 g/Kg of body weight.

In another embodiment the effective amount of the alkylglycerol or an analog thereof is 300 mg per day.

In yet another embodiment, the subject invention provides a method of treating a malignant tumor comprising of malignant tumor cells in a subject by administering to the subject a compound having the formula:

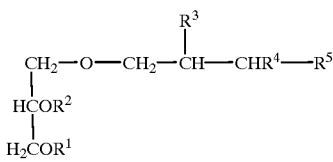

where $R^1$ and $R^2$ are the same or different and each is selected from the group consisting of hydrogen and aliphatic acyl groups of at most 24 carbon atoms, one of $R^3$ and $R^4$ is hydrogen and the other is selected from the group consisting of straight, branched, saturated and unsaturated alkoxy groups of at most 7 carbon atoms, and $R^5$ is selected from the group consisting of straight and branched alkyl and alkenyl groups of 4 to 21 carbon atoms; and a chemotherapeutic agent, each in an amount effective to kill malignant tumor cells or inhibit malignant tumor cell proliferation thereby treating the tumor.

In another embodiment, the subject invention provides a method of treating a malignant tumor comprising of malignant tumor cells in a subject by administering to the subject a chemotherapeutic agent, and a fish oil, each in an amount effective to kill malignant tumor cells or inhibit malignant tumor cell proliferation, thereby treating the tumor.

In yet another embodiment the fish oil is docosahexaenoic acid or eicosapentaenoic acid.

As used herein, "malignant" means capable of metastasizing. As used herein, "tumor cells" are cells which originate from a tumor, i.e., from a new growth of different or abnormal tissue. The tumor cells may exist as part of the tumor mass, or may exist as free-floating cells detached from the tumor mass from which they originate.

As used in the subject invention, malignant cells include, but are in no way limited to, melanocarcinoma cells, nasopharyngeal carcinoma cells, lung non-small cell carcinoma cells, lung small cell carcinoma cells, breast cancer cells, urinary bladder carcinoma cells, uterine cervix squamous cell carcinoma cells, endometrial carcinoma cells, colonic carcinoma cells, prostate carcinoma cells, osteocarcinoma cells, rhabdomyosarcoma cells, leukemia cells, lymphoma cells, retinoblastoma cells and choriocarcinoma cells.

The methods of the present invention are useful in the treatment of mammalian tumors, including human tumors. Examples of such tumors include, but are not limited to, adrenocarcinomas, glioblastomas (and other brain tumors), breast, cervical, colorectal, endometrial, gastric, liver, lung (small cell and non-small cell), lymphomas (including non-Hodgkin's, Burkitt's, diffuse large cell, follicular and diffuse Hodgkin's), melanoma (metastatic), neuroblastoma, osteogenic sarcoma, ovarian, retinoblastoma, soft tissue sarcomas, testicular and other tumors which respond to chemotherapy. Thus, the methods of the present invention can be used to treat tumors, including experimentally induced cancer tumors, in any type of mammal including humans, commonly used laboratory animals such as rats, mice, rabbits and dogs, primates such as monkeys, and horses, cats and other animals.

The methods of the present invention can be practiced with any type of chemotherapy agent. In any particular embodiment of the invention, the chemotherapy agent will be selected with reference to factors such as the type of cancer tumor and the efficacy of the chemotherapy agent for treating the cancer tumor involved. The chemotherapy agent may be selected from alkylating agents, antimetabolites, natural products, hormones and antagonists and other types of compounds.

Examples of alkylating agents include, but are not limited to, the nitrogen mustards (i.e. the 2-chloroethylamines) such as, for example, chloromethine, chlorambucil, melphalan, uramustine, mannomustine, extramustine phosphate, mechlor-thaminoxide, cyclophosphamide, ifosamide and trifosfamide; alkylating agents having a substituted aziridine group such as, for example, tretamine, thiotepa, triaziquone and mitomycin; alkylating agents of the alkyl sulfonate type, such as, for example, busulfan, and piposulfan; alkylating N-alkyl-N-nitrosourea derivatives such as, for example, carmustine, lomustine, semustine or streptozotocine; alkylating agents of the mitobronitole, dacarbazine and procarbazine type; and platinum complexes such as, for example, cisplatin and carboplatin.

Examples of antimetabolites include, but are not limited to, folic acid derivatives such as, for example, methotrexate, aminopterin and 3'-dichloromethotrexate; pyrimidine derivatives such as, for example, 5-fluorouracil, floxuridine, tegafur, cytarabine, idoxuridine, and flucytosine; purine derivatives such as, for example, mercaptopurine, thioguanine, azathioprine, tiamiprine, vidarabine, pentostatin and puromycin.

Examples of natural products include, but are not limited to, vinca alkaloids such as for example vinblastine and vincristine; epipodophylotoxins such as, for example, etoposide, and teniposide; antibiotics such as, for example, adrimycin, daunomycin, dactinomycin, daunorubicin, doxorubicin, mithramycin, bleomycin and mitomycin; enzymes such as, for example, L-asparaginase; biological response modifiers such as, for example, alphainterferon; camptothecin; taxol; and retinoids such as retinoic acid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Ten (10) patients were studied. A biopsy was taken from each and analyzed using in vitro cultures.

Experimental Procedures

Method—Fluorescent Cytoprint Assay

The fluorescent cytoprint in vitro assay was designed to measure the effectiveness of specific chemotherapy drugs in destroying individual patients' cancer cells. Tumor tissue samples were "sandwiched" between two thin papers coated with collagen and supported by small grids at the surface of the culture medium. This technique assured the tumor samples, called "micro-organs" (300–500 viable tumor cells having the same structure and function of the original tumor) would be stationary and could be monitored over time under the microscope and photographed. The tissue samples were then exposed to a panel of chemotherapeutic agents and examined to see how many and which micro-organs had been killed. Drugs were also tested in varying concentrations.

Shipping and Handling of Specimen Sample

Each specimen was placed in a tube with transport medium and shipped overnight in a freezer pack to Analytical Biosystems. Upon arrival the specimen was transferred to a laminar flow hood for processing and assay. A sample of 1 gram of viable tumor tissue was sufficient for assay of the treatments at three different concentrations. The specimen was centrifuged, washed with fresh medium, and after mincing, collagenase was added. The culture was then incubated for 18–24 hours.

Culture Set Up

Following the initial incubation, the micro-organ cultures were prepared. Tumor fragments were collected by centrifugation, washed, and resuspended in media. After 30 minutes in the dark, large fragments (100–1500 cells) were planted in a matrix of cellulose fibers impregnated with collagen. These micro-organ cultures were placed on stainless steel screen supports located in each well of a 24-well tissue culture plate. Medium was added so that the culture sat at the liquid gas interface and was fed by capillary action through the cellulose matrix. Cultures were returned to the incubator for 24 hours.

Fluorescent Cytoprinting

Following the 4 hour incubation, the initial cytoprint was prepared. Fluorescein acetate in serum-free medium was added. Viable tumor cell clusters or micro-organs with intact cell membranes retained fluorescein released from the substrate and became fluorescent. After 30 minutes in the dark, cultures were washed and the patterns of fluorescent micro-organs (cytoprints) were recorded photographically under a dissecting microscope. This record served as the baseline, i.e., each culture served as its own baseline when cytoprinting was repeated at the end of the assay period. Cultures were then returned to the medium to allow viable tumor cell clusters to expel the fluorescein.

Drug Treatment

In the initial studies we determined tumor susceptibility following: (a) the addition of lipid-based emulsions, (b) chemotherapeutic agents, and (c) lipid-based emulsions plus chemotherapeutic agents. The drug groups were run concurrently within any one assay. All samples including control (no drug) were carried out in duplicate.

Evaluation and Drug Effects

Cytotoxicity (loss of fluorescent micro-organs) was assessed by comparing photographic and fluorescent cytoprints taken before and after treatment. Results of the cytotoxicity was reported as "sensitive" (greater than 90% cell death); "intermediate" (between 25 and 90% cell death), and "resistant" (less than 25% cell death). Tumor growth and viability was indicated by comparing changes in shape and size of the micro-organs following drug treatment with the initial cytoprints of untreated cultures of the same specimen (control).

The results of these studies allowed us to examine the effects of Alkylglycerols on the viability and susceptibility of breast cancer cells and to determine whether they can serve as an adjuvant to chemotherapeutic agents.

Results

Out of ten patients who received a combination of chemotherapy and alkylglycerols, or methoxyglycerols, six tests resulted in tumor sensitivities at, or above, 90%, compared with only one patient in the group receiving doxorubicin or fluorouracil alone.

In our study group, one patient's tumor tissue sample was inadequate and a test combining doxorubicin, fluorouracil and alkylglycerol was not possible. This patient was also the only individual that showed sensitivity to chemotherapy alone in all groups tested.

Of the nine remaining patients six had sensitivities of 90% or better. In the three patients who did not fit this criteria one patient showed a sensitivity at or above 80% when alkylglycerols were combined with the chemotherapeutic agents, and in the two patients remaining both showed an increased sensitivity to chemotherapy when alkylglycerols were used.

The patients possessed the following characteristics: Six patients had breast cancer, one had metastatic adenocarcinoma of the lung, one had mesothelioma, one had colon cancer, and one had renal cancer.

In the breast cancer group five of the patients in this group had infiltrating ductal carcinoma, and one had adenocarcinoma. Three of the patients with infiltrating ductal carcinoma reached sensitivity levels at or above 90% when chemotherapy was used in combination with alkylglycerols.

Another patient had an improvement in their sensitivity from Resistant to Intermediate, and in one case there was no improvement noted. The patient with adenocarcinoma in this group had an inadequate tissue sample, and we were unable to compare results. One of these patients was also tested with a specific fraction of alkylglycerol, methoxyglycerol. When this compound was added to one of the tumor cultures in combination with doxorubicin the highest response rate was seen, and the tumor went from approximately 90% sensitivity to greater than 90% sensitivity. With fluorouracil alone, the tumor was Resistant, and exhibited Intermediate sensitivity when used in combination with the methoxyglycerol.

In the mesothelioma patient the sample was resistant to all chemotherapeutic agents when given alone. When the tumor was exposed to a combination of doxorubicin and alkylglycerol the tumor response was at 90%.

The second lung cancer patient sample was a metastatic lesion from a primary colon cancer. This sample was Resistant to doxorubicin and showed an Intermediate sensitivity to fluorouracil. When exposed to alkylglycerols the sensitivity increased to Intermediate level in combination with doxorubicin, and further increased to Sensitive in combination with fluorouracil. This was found to be the case in both the mid dose and the high dose groups.

In the clear cell-predominant renal cell carcinoma patient the tumor showed an Intermediate sensitivity to doxorubicin and fluorouracil, and was resistant to an additional chemotherapeutic agent, vinblastine. In the mid dose alkylglycerol/doxorubicin combination, more than 80% of the tumor was killed. However, this did not meet the 90% or better criteria.

Alkylglycerols in combination with chemotherapeutic agents, specifically, doxorubicin (adriamycin) and fluorouracil, inhibit tumor cell growth and augment the cytotoxic effects of chemotherapeutic agents in tumor cell culture. Doxorubicin is believed to work by its ability to penetrate the cell membrane of tumors, ultimately poisoning its target cell. Alkylglycerols, and in particular, the subfraction, methoxyglycerol, concentrate in tumor cells at a rate (one hundred to one thousand times) more than in healthy, normal cells. The addition of alkylglycerols may inhibit tumor cell defenses which would normally restrict the uptake of doxorubicin causing the tumor cell to become more susceptible to the chemotherapeutic agent. They may also prevent replication of tumor cells by altering the structure of the lipid membrane thus causing increased fragility of tumor cells. Further evaluation of the role of alkylglycerols in cancer therapy based on the results of this study may prove beneficial.

Discussion

It has been shown by Das et. al 1992 that dietary ether lipids can be directly utilized by mammals to synthesize membrane alkyl glycerolipids and plasmalogens in most tissues. Several studies have shown that the amount of alkyldiacylglycerols is much higher in neoplastic cells than in normal cells. (Spener, 1983) The amount in tumorous tissue can be 10–100 times higher as compared with normal tissue. The explanation is the tumorous tissue contains extremely low amounts of ether cleavage enzyme.

The German research groups have shown that even alkyllysophospholipids without the 2-methoxy group in the glycerol part can activate macrophages in the bone marrow. This shows that ordinary glycerolethers, after incorporation into phospholipids, can activate the body's immune defense system. The German researchers think that the macrophage stimulating effects of alkyllysophospholipids explain the effect of these substances on tumors and tumor spread. Tumor cells have only a low activity of enzymes which can break down ethers. This means that alkylethers are incorporated into the cell membrane's phospholipids which are then recognized and attacked by macrophages which have a high activity of ether catabolic enzymes.

Since no macrophages were involved in our study on the effects of alkylglycerols on cellular growth in tumor cultures there must also be other explanations for the effects on the tumor cells.

The shark liver oil preparation that we used contained 2-3 percent methoxy-substituted alkylglycerols. The methoxy group may block and disturb the cell membranes more than the ordinary alkylglycerols.

Our theory is that we are dealing with a selective competitive inhibition that is disturbing malignant cells more than normal cells. The effected tumor tissue will then be more easy to treat with cytostatics.

Interactions between different types of alkylglycerols and human neutrophil granulocytes have been studied by Palmblad, Samuelsson and Brohult (1990). Platelet activating factor (PAF) was the most potent with regard to the ability to produce an oxidative response followed by the methoxy-substituted alkylglycerols. The study shows that there is a dissociation between the ability of an alkylglycerol to initiate oxidative and calcium responses, indicating strict structure-activity relationships for the different alkylglycerols studied.

In patients treated with radiation for cancer of the uterine cervix, the protective effect of the mixture of methoxy, substituted and unsubstituted against leucopenia and thrombocytopenia might be due to the unsubstituted alkylglycerols, as a stimulatory effect on the bone marrow has been demonstrated for both chimyl alcohol and batyl alcohol. It has been shown that batyl alcohol promotes the growth of Lactobacillus Lactis (Brohult, 1963), while the methoxy-substituted alkylglycerols have shown an antibiotic effect in vitro against several types of bacteria (Hallgren, 1983). We are thus dealing with different compounds with different working mechanisms. The protective effect against local radiation injuries (Brohult et al., 1977) might be explained by a membrane effect of the alkylglycerols, leading to an increase in the radiation sensitivity of the tumor in relation to the normal tissue.

The methoxy-substituted alkylglycerols have been found to inhibit tumor growth in cultured cells. (Hallgren et al., 1978)

It is notable that the same substance can stimulate both the immune system and inhibit tumors. This has also been shown to be true for alkyllysophospholipids synthesized with a methoxy group in the 2-position of the glycerol part of the molecule. These substances have been studied at the Max-Planck Institute for Immunobiology at Freiburg and at the Department of Haematology and Oncology of the University of Munich. (Berdel et al., 1980, 1981)

In experiments performed at the University of Stockholm it has been shown that 1–0 (2-methoxy) hexadecyl glycerol (see formula below) inhibits growth of human, neuroblastoma cells (SH-SY5Y) and human epithelial cancer cells (HeLa). (Walum et al., 1996)

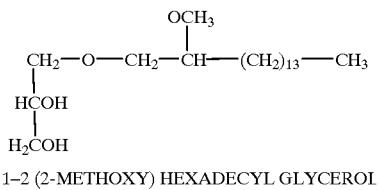

1-2 (2-METHOXY) HEXADECYL GLYCEROL

In summary, the results show that chemotherapeutic agents become more effective when accompanied by the administration of alkylglycerols. The administration of a chemotherapeutic agent together with an alkylglycerol results in tumor cell kill that is higher than the tumor cell kill achieved by administration of each component separately, i.e. the combination has a synergistic effect.

Figure 2:
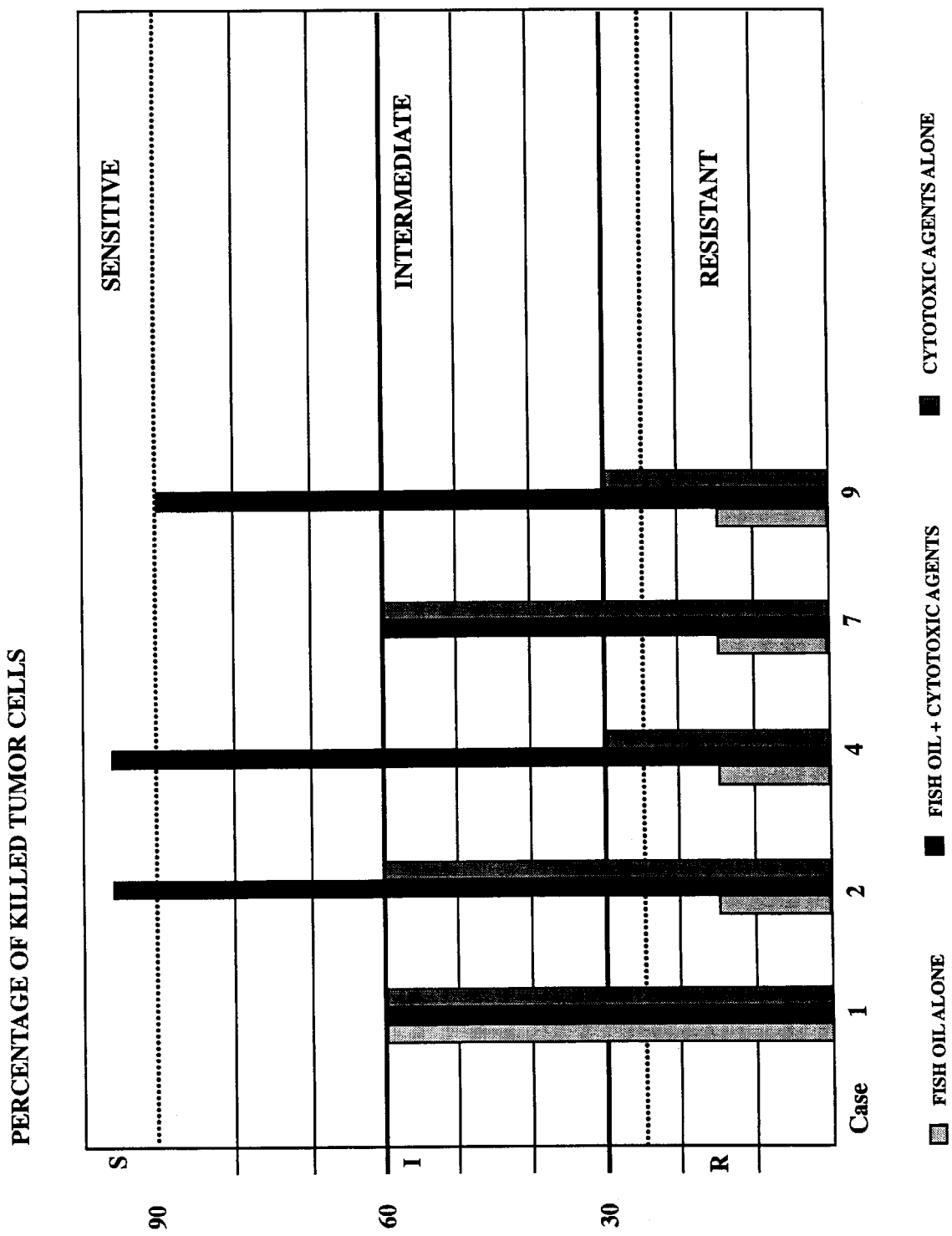
FIG. 2 shows the response of five biopsies to chemotherapeutic agents alone as compared to fish oil alone as compared to the combination of chemotherapeutic agent with the fish oil.

In a similar study, the effectiveness of cytotoxic agents was also enhanced when administration of the cytotoxic agents was accompanied by the administration of fish oil. Using the Fluorescent Cytoprint Assay method, the cytotoxic effect of fish oil, alone and in combination with cytotoxic agents, on tumor tissue of five of the ten study subjects was tested. The results are depicted in FIG. 2.

Four out of the five tumor cell samples showed increased sensitivity to the cytotoxic agents when combined with fish oil, of these, three showed results which indicated 90% cell kill or better. The remaining sample showed an equal sensitivity to fish oil alone, fish oil in combination with cytotoxic agents, and cytotoxic agents alone. The increased sensitivity cases are described below with reference to FIG. 2:

Case 1

Tumor Pathologic Diagnosis: Infiltrating carcinoma Specimen Anatomic Site: Right breast mass Results indicated an equal Intermediate sensitivity to fish oil alone, fish oil in combination with cytotoxic agents, and cytotoxic agents alone.

Case 2

Tumor Pathologic Diagnosis: Infiltrating duct carcinoma, moderately differentiated Specimen Anatomic Site: Right breast Results indicated Resistance to fish oil alone, a better than 90% Sensitivity when the fish oil was combined with cytotoxic agents, and an Intermediate sensitivity to the cytotoxic agents used alone.

Case 4

Tumor Pathologic Diagnosis: Mesothelioma Specimen Anatomic Site: Pleural mass Results indicated Resistance to fish oil alone, a better than 90% Sensitivity when the fish oil was combined with cytotoxic agents, and a Resistance to Intermediate response when the cytotoxic agents were used alone.

Case 7

Tumor Pathologic Diagnosis: Infiltrating ductal carcinoma, grade III Specimen Anatomic Site: Left breast Results indicated Resistance to fish oil alone, and Intermediate sensitivity when fish oil was used with the cytotoxic agents, and an Intermediate sensitivity to the cytotoxic agents alone.

Case 9

Tumor Pathologic Diagnosis: Adenocarcinoma Specimen Anatomic Site: Right lung. Results indicated Resistance to fish oil alone, a 90% Sensitivity when the fish oil was combined with cytotoxic agents, and a Resistance to Intermediate sensitivity to the cytotoxic agents alone.

Three of the five samples showed a remarkably increased percentage of tumor cell kill when the combination of fish oil with the cytotoxic agents was administered, resulting from a significant increase in the sensitivity.

In this study we were able to show that fish oils containing Omega-3 fatty acids were also able to enhance tumor cell kill when combined with chemotherapeutic agents. The amount of fish oils necessary to accomplish this would be 8–20 capsules per day, or an equivalent intravenous amount. The active ingredient Eicosapentaenoic acid (EPA) or Docosahexaenoic Acid (DHA) would need to be in amounts of 2000 mg of EPA or 1500 mg of DHA, not readily available from a human diet. These amounts would be 4–10 times the amount found in a serving of 4 oz. of fish.

References

Alexander, P., Connell, D. I., Brohult, A., and Brohult, S. "Reduction of Radiation Induced Shortening of Life-Span by a Diet Augmented with Alkoxyglycerol Esters and Essential Fatty Acids." Gerontologia (1959) 3:147

Arturson, G. and Lindback, M. "Experiments on the Effect of Batyl Alcohol on the Number of Erythrocytes and Reticulocytes in White Mice." Acta Soc Med Upsalien (1951) 56, 19.

Berdel, W. E., Bausert, W. R., Weltzien, H. V., Modolell, M. I., Widman, K. H., Munder, P. G. "The Influence of Alkyl-lysophospholipids and Lysophospholipid-activated Macrophages on the Development of Metastases of 3-Lewis Lung Carcinoma. Eur J Cancer (1980); 16:1199–1204.

Berdel, W. E., Fink, U., Egger, B., Reichert, A., Munder, P. G., Rastetter, J. "Growth Inhibition of Malignant Hypernephroma Cells by Autologous Lysophospholipid Incubated Macrophages Obtained by a New Method." Anticancer Research (1981) 1:135–40.

Boeryd, B., Hallgren, B. "The Influence of The Lipid Composition of The Feed Given to Mice on the Immunocompetence and Tumor Resistance of the Progeny." Int J Cancer (1980) 26:241–6.

Boeryd, B., Nilsson, T., Lindholm, L., Lange, S., Hallgren, B., Stallberg, G. "Stimulation of Immune Reactivity by Methoxy-Substituted Glycerol Ethers Incorporated into the Feed." Eur J Immunol (1978) 8:678–80.

Brohult, A., Brohult, J., Brohult, S., Joelsson, I. "Effect of Alkoxyglycerols on the Frequencyof Injuries Following Radiation Therapy for Carcinoma of the Uterine Cervix." Acta Obstet Gynecol Scand (1977) 56:441.

Brohult, A., Brohult, J., Brohult, S., Joelsson, I. "Effect of Alkoxyglycerols on the Frequency of Fistulas Following Radiation Therapy for Carcinoma of the Uterine Cervix." Acta Obstet Gynecol Scand (1979) 58:203.

Brohult, A., Brohult, J., Brohult, S., Joelsson, I. "Reduced Mortality in Cancer Patients After Administration of alkoxyglycerols. Acta Obstet Gynecol Scand (1986) 65: 779–85.

Brohult, A., Brohult, J., Brohult, S. "Effect of Irradiation and Alkoxyglycerol Treatment on the Formation of Antibodies after Salmonella Vaccination." Experientia (1972) 28:146.

Brohult, A., Brohult, J., Brohult, S. "Regression of Tumor Growth After Administration of Alkoxyglycerols." Acta Obstet Gynecol Scand (1978) 57:79.

Brohult, A. "Alkoxyglycerols and Their Use in Radiation Treatment." Acta Radiol (1963) Suppl 223.

Brohult, A. and Holmberg, J. "Alkylglycerols in the Treatment of Leucopenia Caused by Irradiation." Nature (1954) 174,1102

Das, A. K., Holmes, R. D., Wilson, G. N., and Hajra, A. K. "Dietary Ether Lipid Incorporation into Tissue Plasmalogens of Humans and Rodents." *Lipids* (1992) 27:401–405

Hallgren, B., Stallberg, G., Boeryd, B. "Occurrence, Synthesis and Biological Effect of Methoxysubstituted Glycerol Ethers." *Progress in Chemistry of Fats and OtherLipids* (1978) 16:45.

Hallgren, B. "Therapeutic Effects of Ether Lipids." in Ether Lipids. (eds. Mangold, H. K. and Paltauf, F.) New York: Academic Press, 1983. 261–275.

Herrmann, B. J., Neumann, H. A. "Cytotoxic Ether Phospholipids" *J Biol Chem* (1986) 261:7742–47.

Horrocks, L. A. Content, Composition and Metabolism of Mammalian Lipids that Contain Ether Groups. Snyder, F., (ed) New York: Ether Lipids. Academic Press, 1972. 177–272.

Palmblad, J., Samuelsson, J. and Brohult, J. "Interactions Between Alkylglycerols and Human Neutrophil Granulocytes." *Scand J Lab Invest* (1990) 50: 363–370

Sandier, O. E. "Some Experimental Studies on the Erythropoietic Effects of Yellow Bone Marrow Extracts and Batyl AlcohoL." *Acta Med Scand* (1949) Suppl. 225:133

Spener, F. "Ether Lipids in Clinical Diagnosis and Medical Research." in Ether lipids. (eds. Mangold, H. K. and Paltauf, F. P.) New York: Academic Press, 1983. 239–259.

Walum, E., Brohult, J., Werner, B. "Effect of 1-0(2-methoxy) Hexadecyl Glycerol on the Growth of Human Neuroblastoma Cells and Human Epithelial Cancer Cells." Inmanuscript, 1996.

What is claimed is:

1. A method of treating a malignant tumor comprising of malignant tumor cells sensitive to the combination below in a subject, which comprises administering to the subject a combination consisting essentially of:

a chemotherapeutic agent; and a shark liver oil, wherein the combination is more effective to kill malignant tumor cells or inhibit malignant tumor cell proliferation than the chemotherapeutic agent alone.

2. The method of claim 1, wherein the subject is a human.

3. The method of claim 1, wherein the chemotherapeutic agent is doxorubicin.

4. The method of claim 1, wherein the administration of the chemotherapeutic agent follows administration of the shark liver oil.

5. The method of claim 1, wherein the chemotherapeutic agent is administered concurrently with the shark liver oil.

6. The method of claim 1, wherein the tumor is infiltrating duct carcinoma, adenocarcinoma or colon cancer.

7. The method of claim 1, wherein the effective amount of the shark liver oil is from about 1 g/Kg of body weight to 10 g/Kg of body weight.

8. The method of claim 1, wherein the effective amount of the shark liver oil is about 300 mg per day.

9. The method of claim 1, wherein the chemotherapeutic agent is an alkylating agent.

10. The method of claim 9, wherein the alkylating agent is selected from the group consisting of chloromethine, chlorambucil, melphalan, uramustine, mannomustine, extramustine phosphate, mechlor-thaminoxide, cyclophosphamide, ifosamide, trifosfamide, tretamine, thiotepa, triaziquone, mitomycin, busulfan, piposulfan, carmustine, lomustine, semustine, streptozotocine, alkylating agents of the mitobronitole, dacarbazine, cisplatin and carboplatin.

11. The method of claim 1, wherein the chemotherapeutic agent is an antimetabolite.

12. The method of claim 11, wherein the antimotabolite is selected from the group consisting of methotrexate, aminopterin, 3'-dichloromethotrexate, 5-fluorouracil, floxuridine, tegafur, cytarabine, idoxuridine, flucytosine; mercaptopurine, thioguanine, azathioprine, tiamiprine, vidarabine, pentostatin and puromycin.

13. The method of claim 1, wherein the chemotherapeutic agent is a natural product.

14. The method of claim 13, wherein the natural product is selected from the group consisting of vinca alkaloids, vinblastine, vincristine, epipodophylotoxins, etoposide, teniposide, adrimycin, daunomycin, dactinomycin, daunorubicin, doxorubicin, mithramycin, bleomycin, mitomycin, L-asparaginase, alphainterferon, camptothecin, taxol, retinoids and retinoic acid.

* * * * *